United States Patent
Morita et al.

(10) Patent No.: US 9,725,396 B2
(45) Date of Patent: Aug. 8, 2017

(54) ACTIVE MATERIAL, AND SODIUM ION BATTERY AND LITHIUM ION BATTERY USING THE SAME

(71) Applicants: Toyota Jidosha Kabushiki Kaisha, Toyota-shi, Aichi-ken (JP); Osaka University, Suita-Shi, Osaka (JP)

(72) Inventors: Yasushi Morita, Nagoya (JP); Shinji Nakanishi, Mishima (JP)

(73) Assignees: Toyota Jidosha Kabushiki Kaisha, Toyota-shi, Aichi-ken (JP); Osaka University, Suita-Shi, Osaka (JP)

( * ) Notice: Subject to any disclaimer, the term of this patent is extended or adjusted under 35 U.S.C. 154(b) by 49 days.

(21) Appl. No.: 14/730,650

(22) Filed: Jun. 4, 2015

(65) Prior Publication Data

US 2015/0357631 A1  Dec. 10, 2015

(30) Foreign Application Priority Data

Jun. 5, 2014 (JP) ................................ 2014-116581

(51) Int. Cl.
*C07C 65/15* (2006.01)
*C07C 65/40* (2006.01)
(Continued)

(52) U.S. Cl.
CPC .............. *C07C 65/15* (2013.01); *C07C 65/40* (2013.01); *H01M 4/60* (2013.01);
(Continued)

(58) Field of Classification Search
None
See application file for complete search history.

(56) References Cited

U.S. PATENT DOCUMENTS

2013/0189571 A1* 7/2013 Abouimrane .......... H01M 4/60
429/188

FOREIGN PATENT DOCUMENTS

| JP | 2007-227186 A | 9/2007 |
| JP | 2009-129742 A | 6/2009 |
| WO | 2013042706 A1 | 3/2013 |

OTHER PUBLICATIONS

STIC Search by O. Darwish.*

* cited by examiner

Primary Examiner — Patrick Ryan
Assistant Examiner — Victoria Lynch
(74) Attorney, Agent, or Firm — Dinsmore & Shohl LLP

(57) ABSTRACT

Provided is an active material used for a sodium ion battery or a lithium ion battery, the active material including: $(COONa)_3$-trioxotriangulene represented by the following Formula (1) or $(COOLi)_3$-trioxotriangulene represented by the following Formula (2).

(1)

(Continued)

-continued
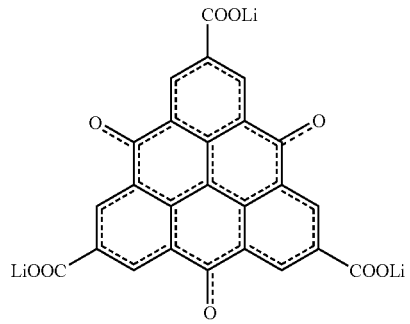
(2)
In Formulae (1) and (2), a double line including a solid line and a broken line represents a single bond or a double bond.
3 Claims, 1 Drawing Sheet
(51) Int. Cl.
    *H01M 4/60*     (2006.01)
    *H01M 10/054*     (2010.01)
    *H01M 10/0525*     (2010.01)
(52) U.S. Cl.
    CPC ....... *C07B 2200/03* (2013.01); *H01M 10/054* (2013.01); *H01M 10/0525* (2013.01)

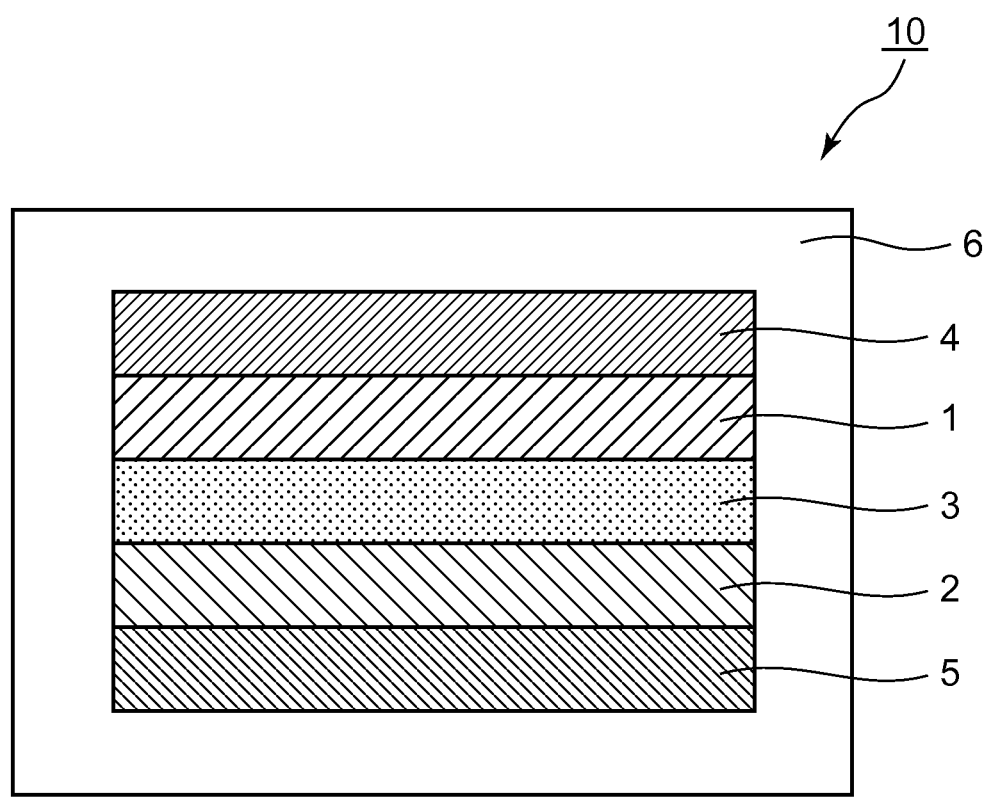

ACTIVE MATERIAL, AND SODIUM ION BATTERY AND LITHIUM ION BATTERY USING THE SAME

INCORPORATION BY REFERENCE

The disclosure of Japanese Patent Application No. 2014-116581 filed on Jun. 5, 2014 including the specification, drawings and abstract is incorporated herein by reference in its entirety.

BACKGROUND OF THE INVENTION

1. Field of the Invention

The present invention relates to an active material capable of improving the capacity retention of a battery.

2. Description of Related Art

Recently, information relating apparatuses and communication apparatuses such as a personal computer, a video camera, or a mobile phone have been rapidly widespread, and accordingly, high importance has been placed on development of a battery used as a power supply of the apparatuses. In addition, in the automobile industry and the like, development of a battery having high output and high capacity for an electric vehicle or a hybrid vehicle has been progressed. In general, a battery includes: a positive electrode active material layer containing a positive electrode active material; a negative electrode active material layer containing a negative electrode active material; and an electrolyte layer formed between the positive electrode active material layer and the negative electrode active material layer.

In order to improve battery performance, an active material used for a battery has been studied in various ways. For example, International Publication WO 2013/042706 discloses $Br_3$-trioxotriangulene having a phenalenyl structure as an active material for a lithium ion battery. In addition, Japanese Patent Application Publication No. 2009-129742 (JP 2009-129742 A) describes that a cyclic compound is used as a negative electrode active material for a sodium ion secondary battery. Further, Japanese Patent Application Publication No. 2007-227186 (JP 2007-227186 A) discloses an organic compound having a phenalenyl structure as an active material for a lithium ion battery.

The present inventors have made a new attempt to use $Br_3$-trioxotriangulene having a phenalenyl structure as an active material not only for a lithium ion battery but also for a sodium ion battery, and have found a new problem in that the capacity retention of the battery is not sufficient.

SUMMARY OF THE INVENTION

The invention has been made to provide an active material capable of improving the capacity retention of a sodium ion battery or a lithium ion battery.

As a result of a thorough investigation for solving the above-described problem, the present inventors have found that, when a trioxotriangulene derivative substituted with COONa or COOLi, which is a new material, is used as an active material for a lithium ion battery or a sodium ion battery, the capacity retention of the battery is high. Based on this finding, the invention has been completed.

That is, according to a first aspect of the invention, there is provided an active material used for a sodium ion battery or a lithium ion battery, the active material including: $(COONa)_3$-trioxotriangulene represented by the following Formula (1) or $(COOLi)_3$-trioxotriangulene represented by the following Formula (2).

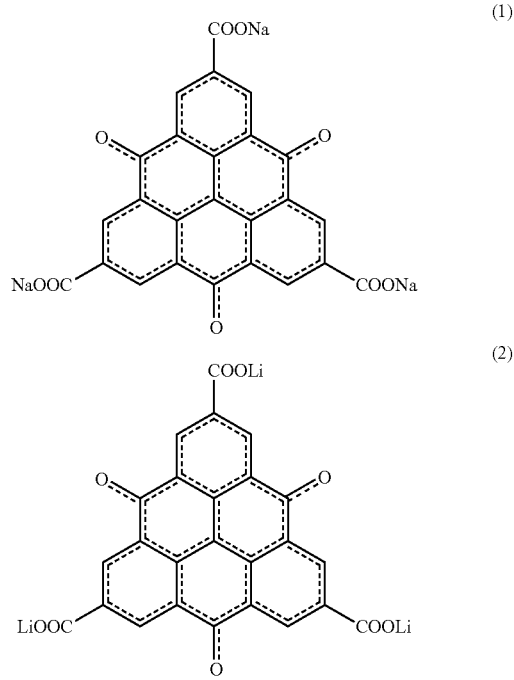

In Formulae (1) and (2), a double line including a solid line and a broken line represents a single bond or a double bond.

According to the invention, the active material includes $(COONa)_3$-trioxotriangulene represented by Formula (1) or $(COOLi)_3$-trioxotriangulene represented by Formula (2). As a result, the active material can improve the capacity retention of a battery.

According to a second aspect of the invention, there is provided a sodium ion battery including: a positive electrode active material layer containing a positive electrode active material; a negative electrode active material layer containing a negative electrode active material; and an electrolyte layer formed between the positive electrode active material layer and the negative electrode active material layer. The positive electrode active material or the negative electrode active material is the above-described active material.

According to the invention, by using the above-described active material, the capacity retention of the sodium ion battery can be improved.

According to a third aspect of the invention, there is provided a lithium ion battery including: a positive electrode active material layer containing a positive electrode active material; a negative electrode active material layer containing a negative electrode active material; and an electrolyte layer formed between the positive electrode active material layer and the negative electrode active material layer. The positive electrode active material or the negative electrode active material is the above-described active material.

According to the invention, by using the above-described active material, the capacity retention of the lithium ion battery can be improved.

According to the invention, an active material capable of improving the capacity retention of a battery can be provided.

BRIEF DESCRIPTION OF THE DRAWING

Features, advantages, and technical and industrial significance of exemplary embodiments of the invention will be described below with reference to the accompanying drawing, in which like numerals denote like elements, and wherein:

FIG. 1 is a schematic cross-sectional diagram showing an example of a sodium ion battery according to a first embodiment of the invention.

DETAILED DESCRIPTION OF EMBODIMENTS

1e;2qHereinafter, an active material, a sodium ion battery, and a lithium ion battery according to the invention will be described in detail.

A. Active Material

First, an active material according to an embodiment of the invention will be described. The active material according to the embodiment is used for a sodium ion battery or a lithium ion battery, the active material including: $(COONa)_3$-trioxotriangulene represented by the following Formula (1) or $(COOLi)_3$-trioxotriangulene represented by the following Formula (2).

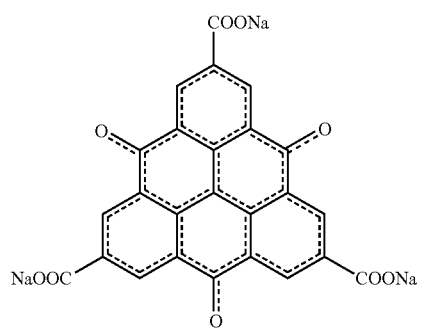

(1)

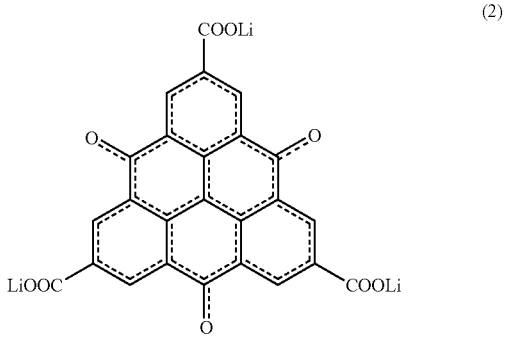

In Formulae (1) and (2), a double line including a solid line and a broken line represents a single bond or a double bond.

Here, "$(COONa)_3$-trioxotriangulene" represented by Formula (1) contains trioxotriangulene as a base material, and examples thereof include a neutral radical compound represented by the following Formula (1-1), an anion compound represented by the following Formula (1-2), a radical dianion compound represented by the following Formula (1-3), a diradical trianion compound represented by the following Formula (1-4), and a radical tetraanion compound represented by the following Formula (1-5).

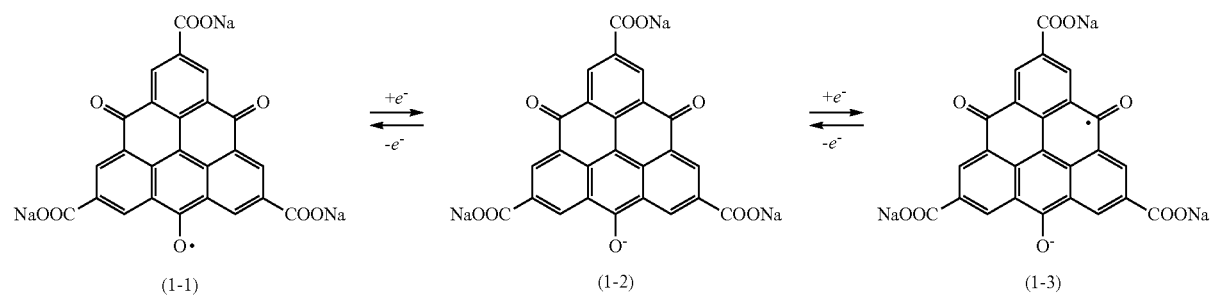

In addition, "(COOLi)$_3$-trioxotriangulene" represented by Formula (2) contains trioxotriangulene as a base material, and examples thereof include a neutral radical compound represented by the following Formula (2-1), an anion compound represented by the following Formula (2-2), a radical dianion compound represented by the following Formula (2-3), a diradical trianion compound represented by the following Formula (2-4), and a radical tetraanion compound represented by the following Formula (2-5).

battery includes: (COONa)$_3$-TOT or (COOLi)$_3$-TOT. As a result, a battery having high output can be obtained using the active material. The reason is presumed to be as follows. That is, in an active material of the related art, a storing/releasing reaction of sodium ions or lithium ions occurs in a structure of the active material; whereas, in the active material according to the embodiment, a storing/releasing reaction of sodium ions or lithium ions occurs on a surface of the active material (radical reaction). Therefore, in the

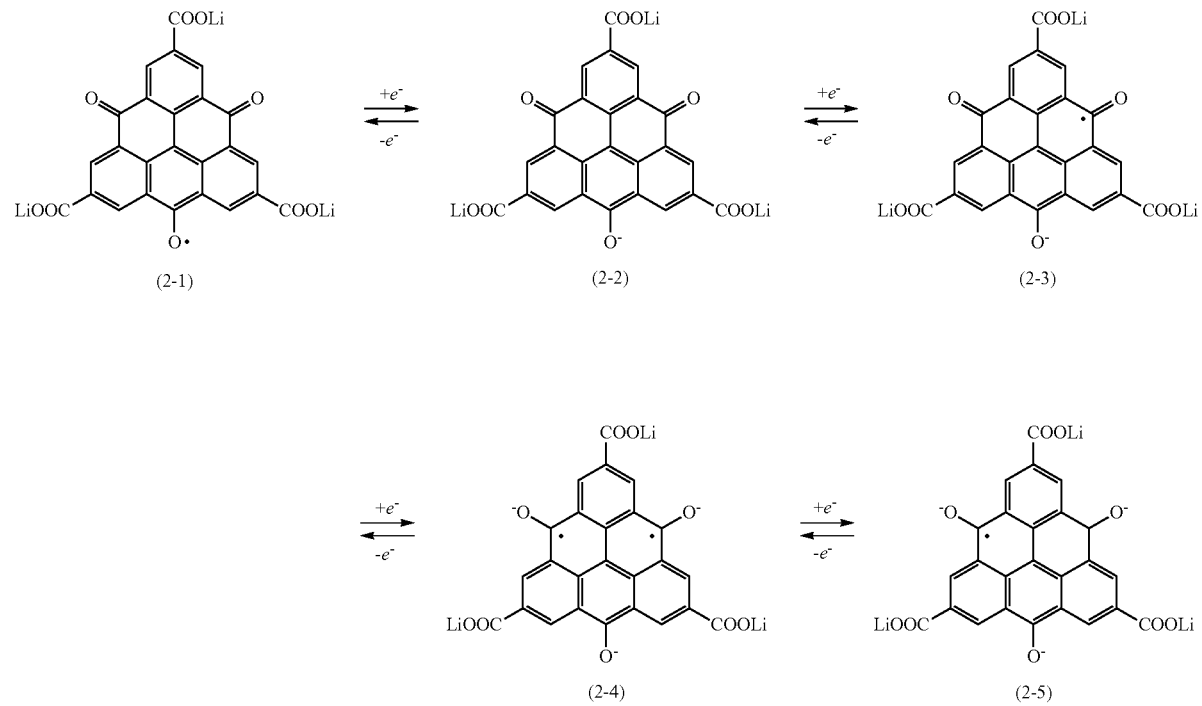

Hereinafter, trioxotriangulene will also be abbreviated as "TOT".

According to the embodiment of the invention, the active material used for a sodium ion battery or a lithium ion battery includes: (COONa)$_3$-TOT or (COOLi)$_3$-TOT. As a result, the capacity retention of the battery can be improved. The reason is presumed to be as follows. First, some of the reasons why the capacity retention of a sodium ion battery or a lithium ion battery is decreased are presumed to be as follows. While a battery is repeatedly charged and discharged, an active material is eluted to an electrolyte layer, the active material eluted to the electrolyte layer is reprecipitated on a surface of an electrode layer as a counter electrode to form a high-resistance layer thereon, and cycle characteristics are decreased. An organic neutral radical compound such as TOT is generally known to have high stability. Specifically, TOT having a planar structure is stably present in a multi-layer state.

(COONa)$_3$-TOT and (COOLi)$_3$-TOT included in the active material according to the embodiment of the invention are particularly hardly decomposed compounds among a group of neutral radical compounds and form a strong intermolecular network when in a crystal state. As a result, it is considered that the capacity retention of a battery can be improved.

Further, according to the embodiment of the invention, the active material used for a sodium ion battery or a lithium ion storing/releasing reaction of the embodiment, the reaction rate can be increased to be faster than that of the storing/releasing reaction occurring between the active material of the related art and sodium ions or lithium ions. As a result, it is considered that a battery having high output can be obtained.

The active material according to the embodiment may be used as an active material for a sodium ion battery or as an active material for a lithium ion battery. In addition, the active material according to the embodiment may be used as a positive electrode active material or a negative electrode active material.

A shape of the active material according to the embodiment is preferably particulate. In addition, the average particle size (D$_{50}$) of the active material is, for example, preferably in a range of 1 nm to 100 μm and more preferably in a range of 10 nm to 30 μm.

A synthesis method of the active material according to the embodiment is not particularly limited as long as the above-described active material can be obtained using the method. For example, the following method can be adopted.

(COONa)$_3$-TOT and (COOLi)$_3$-TOT can be synthesized, for example, using the following method.

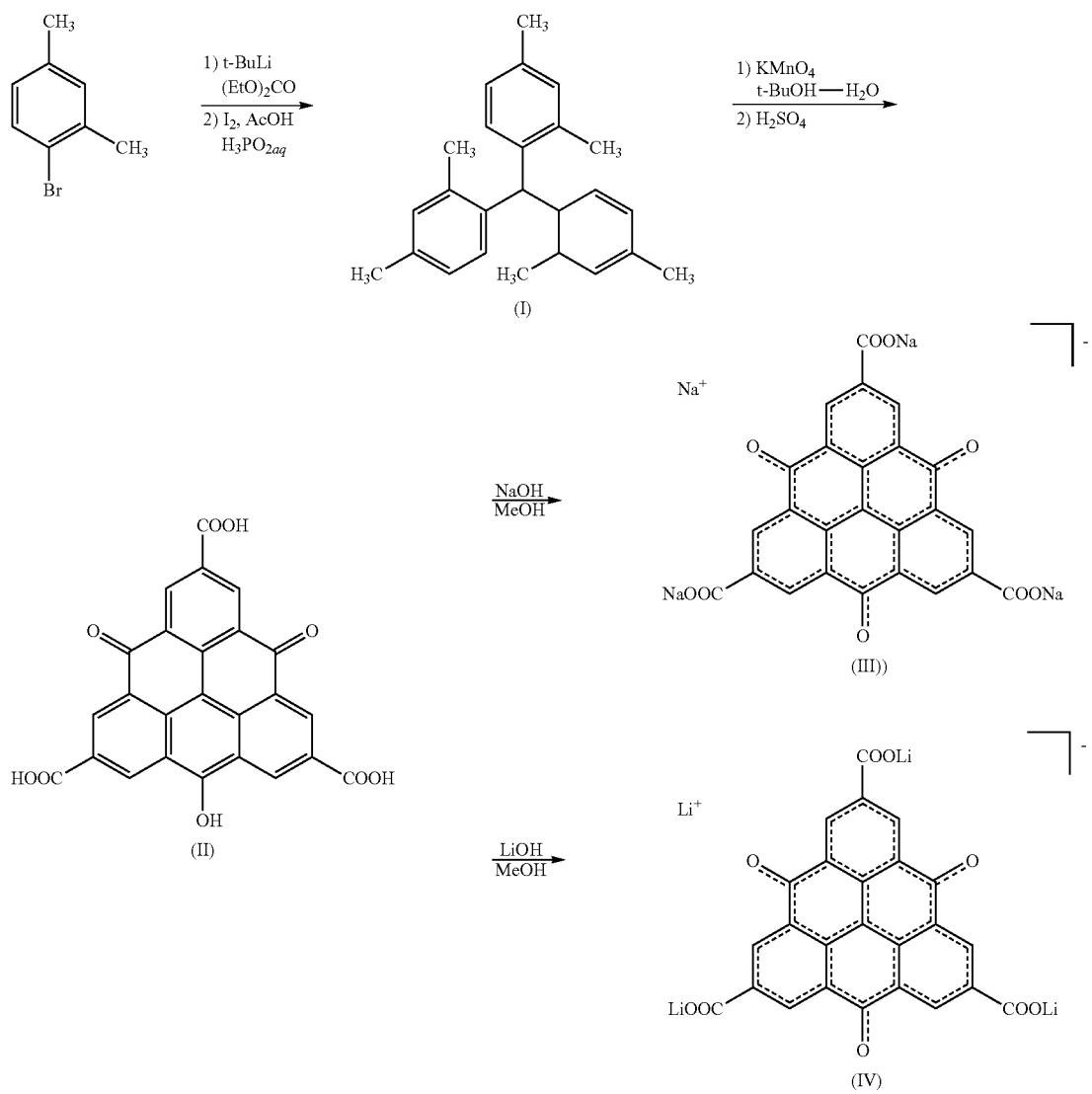

In the synthesis method, a synthesis method of a compound represented by Formula (I) is as follows. First, 2,4-dimethylbromobenzene (24 ml, 0.176 mol) is treated with 1.63 M t-BuLi (216 ml, 0.352 mol), and diethyl carbonate (7 ml, 58 mmol) is added thereto. Next, triarylmethanol (13 g, 65%) is obtained after extraction using an organic solvent, washing with water, and distillation under reduced pressure. This material (10 g, 29 mmol) is stirred at room temperature in acetic acid (300 ml) and an hypophosphoric acid aqueous solution (45 ml). Next, the obtained solution is treated with iodine (7.3 g, 29 mmol), and the obtained white precipitate is separated by filtration. As a result, a compound (5.4 g, 57%) represented by Formula (I) can be obtained.

In the synthesis method, a synthesis method of a compound represented by Formula (II) is as follows. The compound (5.0 g, 15 mmol) represented by Formula (I) is mixed with t-butylalcohol (200 ml) and water (200 ml), and the obtained mixture is treated with potassium permanganate (35.5 g, 225 mmol). After cooling, a NaOH aqueous solution (50 ml) is added to the mixture, and the obtained precipitate is separated by filtration. Next, hydrochloric acid (50 ml) is added to the precipitate to adjust the pH thereof to 1. Ethyl acetate is extracted and then is concentrated under reduced pressure to obtain an oxide (8.1 g, 93%) as a white powder. This material (5 g, 9.8 mmol) is treated with concentrated sulfuric acid (50 ml), and water is added thereto. The obtained solid matter is separated by filtration and is dried in a vacuum. As a result, a compound (5 g, crude yield) represented by Formula (II) can be obtained.

In the synthesis method, a synthesis method of a compound represented by Formula (III) is as follows. The compound (5 g, crude yield) represented by Formula (II) is treated with sodium hydroxide (0.4 g) in methanol (1.0 g, 2.2 mmol). As a result, a compound (0.85 g, 75%) represented by Formula (III) can be obtained. The result of $^1$H-NMR measurement is as follows: $^1$H-NMR (500 MHz, DMSO-d6) δ 9.23 (s, 6H); Anal calcd for C25H20O16Na4(H2O)7: C, 44.93; H, 3.02; N, 0.00. Found: C, 44.94; H, 2.87; N, 0.00.

In the synthesis method, a synthesis method of a compound represented by Formula (IV) is as follows. The compound (5 g, crude yield) represented by Formula (II) is treated with lithium hydroxide (0.8 g) in methanol (1.0 g, 2.2 mmol). As a result, a compound (2.0 g, 95%) represented by Formula (III) can be obtained. The result of $^1$H-NMR measurement is as follows: $^1$H-NMR (500 MHz, DMSO-d6) δ 9.27 (s, 6H).

B. Sodium Ion Battery

A sodium ion battery according to the first embodiment of the invention includes: a positive electrode active material layer containing a positive electrode active material; a negative electrode active material layer containing a negative electrode active material; and an electrolyte layer formed between the positive electrode active material layer and the negative electrode active material layer, in which the positive electrode active material or the negative electrode active material is the above-described active material.

FIG. 1 is a schematic cross-sectional diagram showing an example of the sodium ion battery according to the first embodiment. A sodium ion battery 10 shown in FIG. 1 includes: a positive electrode active material layer 1; a negative electrode active material layer 2; an electrolyte layer 3 that is formed between the positive electrode active material layer 1 and the negative electrode active material layer 2; a positive electrode current collector 4 that collects the current of the positive electrode active material layer 1; a negative electrode current collector 5 that collects the current of the negative electrode active material layer 2; and a battery case 6 that accommodates these members.

According to the first embodiment, by using the above-described active material, the capacity retention of the sodium ion battery can be improved. Hereinafter, each configuration of the sodium ion battery according to the first embodiment will be described.

1. Positive Electrode Active Material Layer

First, the positive electrode active material layer according to the first embodiment will be described. The positive electrode active material layer according to the first embodiment contains at least the positive electrode active material. In addition to the positive electrode active material, the positive electrode active material layer may further contain at least one of a conductive material, a binder, and a solid electrolyte material.

In the first embodiment, the positive electrode active material may be the active material described above in "A. Active Material". On the other hand, when the above-described active material is used as the negative electrode active material, a commonly-used active material may be used as the positive electrode active material. Examples of the positive electrode active material include a layered active material, a spinel-type active material, and an olivine-type active material. Specific examples of the positive electrode active material include $NaFeO_2$, $NaNiO_2$, $NaCoO_2$, $NaMnO_2$, $NaVO_2$, $Na(Ni_xMn_{1-x})O_2$ (0<X<1), $Na(Fe_xMn_{1-x})O_2$ (0<X<1), $NaVPO_4F$, $Na_2FePO_4F$, and $Na_3V_2(PO_4)_3$.

The conductive material is not particularly limited as long as it has desired electron conductivity, and for example, a carbon material may be used. Examples of the carbon material include acetylene black, Ketjen black, carbon black, coke, carbon fiber, and graphite. In addition, the material of the binder is not particularly limited as long as it is chemically and electrically stable, and examples thereof include fluorine-based binders such as polyvinylidene fluoride (PVDF) and polytetrafluoroethylene (PTFE); and rubber-based binders such as styrene-butadiene rubber. In addition, the solid electrolyte material is not particularly limited as long as it has desired ion conductivity, and examples thereof include an oxide solid electrolyte material and a sulfide solid electrolyte material. The solid electrolyte material will be described in detail below in "3. Electrolyte Layer".

A shape of the positive electrode active material is preferably particulate. In addition, the average particle size ($D_{50}$) of the positive electrode active material is, for example, preferably in a range of 1 nm to 100 μm and more preferably in a range of 10 nm to 30 μm. In addition, the higher the content of the positive electrode active material in the positive electrode active material layer, the better from the viewpoint of capacity. For example, the content of the positive electrode active material in the positive electrode active material layer is preferably in a range of 60 wt % to 99 wt % and more preferably in a range of 70 wt % to 95 wt %. In addition, the thickness of the positive electrode active material layer largely varies depending on the configuration of a battery, but is, for example, preferably in a range of 0.1 μm to 1000 μm.

2. Negative Electrode Active Material Layer

Next, the negative electrode active material layer according to the first embodiment will be described. The negative electrode active material layer according to the first embodiment contains at least the negative electrode active material. In addition to the negative electrode active material, the negative electrode active material layer may further contain at least one of a conductive material, a binder, and solid electrolyte material.

In the first embodiment, the negative electrode active material may be the active material described above in "A. Active Material". On the other hand, when the above-described active material is used as the positive electrode active material, a commonly-used active material may be used as the negative electrode active material. In this case, as the negative electrode active material, an active material having lower potential than that of the above-described active material is necessarily used. Further, when the above-described active material is $(COOLi)_3$-TOT, the active material does not contain Na. Therefore, it is preferable that the negative electrode active material contains Na. That is, a Na-containing active material such as Na metal or a Na alloy is preferably used as the negative electrode active material.

In addition, the higher the content of the negative electrode active material in the negative electrode active material layer, the better from the viewpoint of capacity. For example, the content of the negative electrode active material is preferably in a range of 60 wt % to 99 wt % and more preferably in a range of 70 wt % to 95 wt %. In addition, the thickness of the negative electrode active material layer largely varies depending on the configuration of a battery, but is, for example, preferably in a range of 0.1 μm to 1000 μm.

3. Electrolyte Layer

Next, the electrolyte layer according to the first embodiment will be described. The electrolyte layer according to the first embodiment is formed between the positive electrode active material layer and the negative electrode active material layer. Through an electrolyte contained in the electrolyte layer, the positive electrode active material and the negative electrode active material are ionically conductive therebetween. The form of the electrolyte layer is not particularly limited, and examples thereof include a liquid electrolyte layer, a gel electrolyte layer, and a solid electrolyte layer.

Typically, the liquid electrolyte layer is formed using a nonaqueous electrolytic solution. Typically, the nonaqueous electrolytic solution contains a sodium salt and a nonaqueous solvent. Examples of the sodium salt include inorganic sodium salts such as $NaPF_6$, $NaBF_4$, $NaClO_4$, and $NaAsF_6$; and organic sodium salts such as $NaCF_3SO_3$, $NaN(CF_3SO_2)_2$, $NaN(C_2F_5SO_2)_2$, and $NaC(CF_3SO_2)_3$. Examples of the nonaqueous solvent include ethylene carbonate (EC), propylene carbonate (PC), dimethyl carbonate (DMC), diethyl carbonate (DEC), ethyl methyl carbonate (EMC), butylene carbonate (BC), fluoroethylene carbonate (FEC), γ-butyrolactone, sulfolane, acetonitrile, 1,2-dimethoxymethane, 1,3-dimethoxypropane, diethyl ether, tetrahydrofuran, 2-methyltetrahydrofuran, and arbitrary mixtures thereof. A concentration of the sodium salt in the nonaqueous electrolytic solution is, for example, preferably in a range of 0.3 mol/L to 5 mol/L and more preferably in a range of 0.8 mol/L to 1.5 mol/L. When the concentration of the sodium salt is excessively low, the capacity may decrease during high-rate charging and discharging. When the concentration of the sodium salt is excessively high, the viscosity increases, and thus the capacity may decrease at a low temperature. In the first embodiment, as the nonaqueous electrolytic solution, for example, a low volatility liquid such as an ionic liquid may be used as the nonaqueous electrolytic solution.

The gel electrolyte layer can be obtained by adding a polymer to the nonaqueous electrolytic solution to be gelled. Specifically, the gelation can be performed by adding a polymer such as a polyethylene oxide (PEO), polyacrylonitrile (PAN), or polymethyl methacrylate (PMMA) to the nonaqueous electrolytic solution.

The solid electrolyte layer is formed using a solid electrolyte material. In addition, the solid electrolyte material is not particularly limited as long as it has Na ion conductivity, and examples thereof include an oxide solid electrolyte material and a sulfide solid electrolyte material. Examples of the oxide solid electrolyte material include $Na_3Zr_2Si_2PO_{12}$ and β-alumina solid electrolyte (for example, $Na_2O$-$11Al_2O_3$). Examples of the sulfide solid electrolyte material include $Na_2S$—$P_2S_5$.

In addition, the solid electrolyte material according to the first embodiment may be amorphous or crystalline. In addition, a shape of the solid electrolyte material is preferably particulate. In addition, the average particle size ($D_{50}$) of the solid electrolyte material is, for example, preferably in a range of 1 nm to 100 μm and more preferably in a range of 10 nm to 30 μm.

In addition, the thickness of the electrolyte layer largely varies depending on the kind of electrolyte and the configuration of a battery, but is, for example, preferably in a range of 0.1 μm to 1000 μm and more preferably 0.1 μm to 300 μm.

4. Other Configurations

The sodium ion battery according to the first embodiment includes at least the negative electrode active material layer, the positive electrode active material layer, and the electrolyte layer described above. Typically, the sodium ion battery further includes the positive electrode current collector that collects the current of the positive electrode active material layer; and the negative electrode current collector that collects the current of the negative electrode active material layer. Examples of the current collector include SUS, aluminum, copper, nickel, iron, titanium, and carbon. In addition, the sodium ion battery according to the first embodiment may further include a separator that is formed between the positive electrode active material layer and the negative electrode active material layer because a battery having higher safety can be obtained.

5. Sodium Ion Battery

In addition, the sodium ion battery according to the first embodiment may be a primary battery or a secondary battery. However, the sodium ion battery is preferably a secondary battery because it can be repeatedly charged and discharged and is useful as, for example, a vehicle-mounted battery. In addition, examples of the sodium ion battery according to the first embodiment include a coin type, a laminate type, a cylindrical type, and a square type. In addition, a method of manufacturing the sodium ion battery is not particularly limited, and a common method of manufacturing a sodium ion battery can be adopted.

C. Lithium Ion Battery

A lithium ion battery according to a second embodiment of the invention includes: a positive electrode active material layer containing a positive electrode active material; a negative electrode active material layer containing a negative electrode active material; and an electrolyte layer formed between the positive electrode active material layer and the negative electrode active material layer, in which the positive electrode active material or the negative electrode active material is the above-described active material. As a specific structure of the lithium ion battery, the same structure as that of the sodium ion battery described in "B. Sodium Ion Battery" can be adopted, and thus the description thereof will not be repeated.

According to the second embodiment, by using the above-described active material, the capacity retention of the battery can be improved. Hereinafter, each configuration of the lithium ion battery according to the second embodiment will be described.

1. Positive Electrode Active Material Layer

First, the positive electrode active material layer of the second embodiment will be described. The positive electrode active material layer according to the second embodiment contains at least the positive electrode active material. In addition to the positive electrode active material, the positive electrode active material layer may further contain at least one of a conductive material, a binder, and a solid electrolyte material.

In the second embodiment, the positive electrode active material may be the active material described above in "A. Active Material". On the other hand, when the above-described active material is used as the negative electrode active material, a commonly-used active material may be used as the positive electrode active material. Examples of the positive electrode active material include a layered rock-salt type active material such as $LiCoO_2$, $LiMnO_2$, $LiNiO_2$, $LiVO_2$, or $LiNi_{1/3}Co_{1/3}M_{1/3}O_2$; a spinel-type active material such as $LiMn_2O_4$ or $Li(Ni_{0.5}Mn_{1.5})O_4$; and an olivine-type active material such as $LiFePO_4$, $LiMnPO_4$, $LiNiPO_4$, or $LiCuPO_4$.

Regarding the conductive material, the shape of the positive electrode active material, the average particle size ($D_{50}$), the content of the positive electrode active material in the positive electrode active material layer, and the thickness of the positive electrode active material layer, the same configurations as those of the positive electrode active material layer of the sodium ion battery described in "B. Sodium Ion Battery; 1. Positive Electrode Active Material" can be adopted, and thus the description thereof will not be repeated.

2. Negative Electrode Active Material Layer

Next, the negative electrode active material layer according to the second embodiment will be described. The negative electrode active material layer according to the second embodiment contains at least the negative electrode active material. In addition to the negative electrode active material, the negative electrode active material layer may further contain at least one of a conductive material, a binder, and solid electrolyte material.

In the second embodiment, the negative electrode active material may be the active material described above in "A. Active Material". On the other hand, when the above-described active material is used as the positive electrode active material, a commonly-used active material may be used as the negative electrode active material. In this case, as the negative electrode active material, an active material having lower potential than that of the above-described active material is necessarily used. Further, when the above-described active material is (COONa)$_3$-TOT, the active material does not contain Li. Therefore, it is preferable that the negative electrode active material contains Li. That is, as the negative electrode active material, lithium metal, a lithium alloy, a metal oxide containing lithium, a metal sulfide containing lithium, or a metal nitride containing lithium is preferably used.

Regarding the content of the negative electrode active material in the negative electrode active material layer, and the thickness of the negative electrode active material layer, the same configurations as those of the negative electrode active material layer of the sodium ion battery described in "B. Sodium Ion Battery; 1. Negative Electrode Active Material" can be adopted, and thus the description thereof will not be repeated.

3. Electrolyte Layer

Next, the electrolyte layer according to the second embodiment will be described. The electrolyte layer according to the second embodiment is formed between the positive electrode active material layer and the negative electrode active material layer. Through an electrolyte contained in the electrolyte layer, the positive electrode active material and the negative electrode active material are ionically conductive therebetween. The form of the electrolyte layer is not particularly limited, and examples thereof include a liquid electrolyte layer, a gel electrolyte layer, and a solid electrolyte layer.

Typically, the liquid electrolyte layer is formed using a nonaqueous electrolytic solution. Typically, the nonaqueous electrolytic solution contains a lithium salt and a nonaqueous solvent. Examples of the lithium salt include inorganic lithium salts such as LiPF$_6$, LiBF$_4$, LiClO$_4$, and LiAsF$_6$; and organic lithium salts such as LiCF$_3$SO$_3$, LiN(CF$_3$SO$_2$)$_2$, LiN(C$_2$F$_5$SO$_2$)$_2$, and LiC(CF$_3$SO$_2$)$_3$. Examples of the non-aqueous solvent include ethylene carbonate (EC), propylene carbonate (PC), dimethyl carbonate (DMC), diethyl carbonate (DEC), ethyl methyl carbonate (EMC), butylene carbonate (BC), γ-butyrolactone, sulfolane, acetonitrile, 1,2-dimethoxymethane, 1,3-dimethoxypropane, diethyl ether, tetrahydrofuran, 2-methyltetrahydrofuran, and mixtures thereof. The concentration of the lithium salt in the nonaqueous electrolytic solution is, for example, in a range of 0.5 mol/L to 3 mol/L.

The gel electrolyte layer can be obtained by adding a polymer to the nonaqueous electrolytic solution to be gelled. Specifically, the gelation can be performed by adding a polymer such as a polyethylene oxide (PEO), polyacrylonitrile (PAN), or polymethyl methacrylate (PMMA) to the nonaqueous electrolytic solution.

The solid electrolyte layer is formed using a solid electrolyte material. Examples of the solid electrolyte material include an oxide solid electrolyte material and a sulfide solid electrolyte material. Examples of an oxide solid electrolyte material having Li ion conductivity include Li$_{1+x}$Al$_x$Ge$_{2-x}$(PO$_4$)$_3$ (0≤x≤2), Li$_{1+x}$Al$_x$Ti$_{2-x}$(PO$_4$)$_3$ (0≤x≤2), LiLaTiO (for example, Li$_{0.34}$La$_{0.51}$TiO$_3$), LiPON (for example, Li$_{2.9}$PO$_{3.3}$N$_{0.46}$), and LiLaZrO (for example, Li$_7$La$_3$Zr$_2$O$_{12}$). On the other hand, examples of a sulfide solid electrolyte material having Li ion conductivity include a Li$_2$S—P$_2$S$_5$ compound, a Li$_2$S—SiS$_2$ compound, and a Li$_2$S—GeS$_2$ compound.

In addition, the solid electrolyte material according to the second embodiment may be amorphous or crystalline. Regarding the shape of the solid electrolyte material, the average particle size (D$_{50}$), and the thickness of the electrolyte layer, the same configurations as those of the electrolyte layer of the sodium ion battery described in "B. Sodium Ion Battery; 3. Electrolyte Layer" can be adopted, and thus the description thereof will not be repeated.

4. Other Configurations

The lithium ion battery according to the second embodiment includes at least the negative electrode active material layer, the positive electrode active material layer, and the electrolyte layer described above. Typically, the sodium ion battery further includes the positive electrode current collector that collects the current of the positive electrode active material layer; and the negative electrode current collector that collects the current of the negative electrode active material layer. Examples of the current collector include SUS, aluminum, copper, nickel, iron, titanium, and carbon. The lithium ion battery according to the second embodiment may further include a separator that is formed between the positive electrode active material layer and the negative electrode active material layer. A battery having higher safety can be obtained.

5. Lithium Ion Battery

In addition, the lithium ion battery according to the second embodiment may be a primary battery or a secondary battery. However, the lithium ion battery is preferably a secondary battery because it can be repeatedly charged and discharged and is useful as, for example, a vehicle-mounted battery. In addition, examples of the lithium ion battery according to the second embodiment include a coin type, a laminate type, a cylindrical type, and a square type. In addition, a method of manufacturing the lithium ion battery is not particularly limited, and a common method of manufacturing a lithium ion battery can be adopted.

The invention is not particularly limited to the above-described embodiments. The embodiments are exemplary.

Hereinafter, the invention will be described in more detail using Examples.

Examples 1 and 2, Comparative Examples 1 and 2

(Preparation of Active Material Layer)

An active material ((COONa)$_3$-TOT represented by the following Formula (a), (COOLi)$_3$-TOT represented by the following Formula (b), Bra-TOT represented by the following Formula (c), or Cl$_3$-TOT represented by the following Formula (d)), acetylene black (AB) as a conductive material, and polyvinylidene fluoride (PVDF) were mixed with each other at a ratio (active material:AB:PVDF) of 10:80:10 (wt %) to form an active material layer on a working electrode side. In addition, an active material layer on a counter electrode side was obtained using Li metal.

(a) 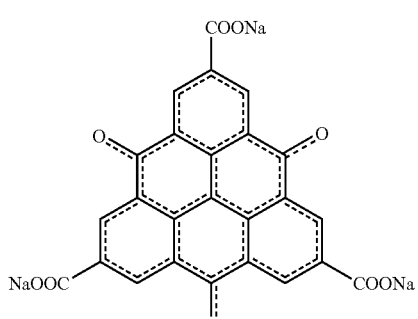

(b) 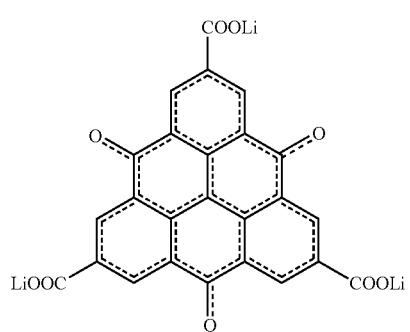

(c) 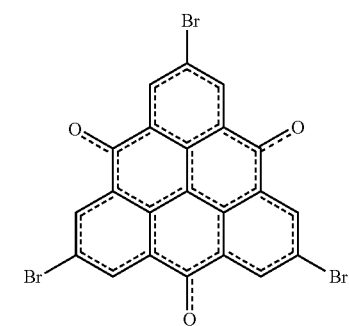

(d) 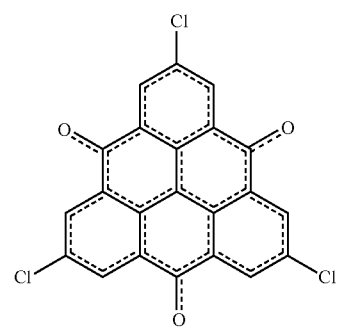

(Preparation of Electrolyte Layer)

Ethylene carbonate (EC), diethyl carbonate (DEC), and dimethyl carbonate (DMC) were mixed with each other at a ratio (EC:DEC:DMC) of 1:1:2 (vol %), and the mixture was further mixed with 1M $LiPF_6$ to prepare an electrolytic solution.

(Preparation of Lithium Ion Battery)

A coin type lithium ion battery including the above-described active material layer, an electrolyte layer, and a separator was prepared. As the separator, a polyolefin (PE or PP) microporous membrane was used.

Examples 3 and 4, Comparative Example 3 and 4

Lithium ion batteries were prepared by the same procedure as that of Examples 1 and 2 and Comparative Examples 1 and 2, except that ethylene carbonate (EC) and ethyl methyl carbonate (EMC) were mixed with each other at a ratio (EC:EMC) of 3:7 (vol %), and the mixture was further mixed with 1M $LiN(CF_3SO_2)_2$ to prepare an electrolytic solution.

[Evaluation 1]

(Evaluation of Capacity Retention of Lithium Ion Battery)

The lithium ion batteries were driven under the following conditions.

Charging: CC 4V 1 C (220 mAh/g=1 C)

Discharging: CC 1V 1 C (220 mAh/g=1 C)

Temperature: 25° C.

As shown in Table 1, the following results were obtained. In Examples 1 and 2, the capacity retention was improved as compared to Comparative Examples 1 and 2. In Examples 3 and 4 in which the material of the electrolytic solution was changed, the capacity retention was improved as compared to Comparative Examples 3 and 4. In addition, in Comparative Examples 1 to 4, the color of the separator after battery decomposition was changed; whereas, in Examples 1 to 4, the color of the separator after battery decomposition was not changed. As a result, in Comparative Examples 1 to 4, the active material was eluted to the electrolytic solution; whereas, in Examples 1 to 4, the active material was not eluted to the electrolytic solution. The capacity retention values shown in Table 1 are the value obtained after 100 cycles.

| | Active Material Layer | | | | Change of Color |
|---|---|---|---|---|---|
| | Working Electrode Side | Counter Electrode Side | Electrolytic Solution | Capacity Retention (%) | of Separator after Battery Decomposition |
| Example 1 | $(COONa)_3$-TOT | Li Metal | EC + DEC + DMC, 1M $LiPF_6$ | 91 | Not Changed |
| Example 2 | $(COOLi)_3$-TOT | | | 89 | |
| Comparative Example 1 | $Br_3$-TOT | | | 72 | Changed |
| Comparative Example 2 | $Cl_3$-TOT | | | 65 | |

-continued

| | Active Material Layer | | | Capacity | Change of Color of Separator |
|---|---|---|---|---|---|
| | Working Electrode Side | Counter Electrode Side | Electrolytic Solution | Retention (%) | after Battery Decomposition |
| Example 3 | (COONa)$_3$-TOT | | EC + EMC, 1M LiN(CF$_3$SO$_2$)$_2$ | 88 | Not Changed |
| Example 4 | (COOLi)$_3$-TOT | | | 87 | |
| Comparative Example 3 | Br$_3$-TOT | | | 68 | Changed |
| Comparative Example 4 | Cl$_3$-TOT | | | 62 | |

Examples 5 and 6, Comparative Example 5 and 6

Sodium ion batteries were prepared by the same procedure as that of Examples 1 and 2 and Comparative Examples 1 and 2, except that Na metal was used for the active material layer on a counter electrode side; and ethylene carbonate (EC) and diethyl carbonate (DEC) were mixed with each other at a ratio (EC:DEC) of 1:1 (vol %), and the mixture was further mixed with 1M NaPF$_6$ to prepare an electrolytic solution.

Examples 7 and 8, Comparative Example 7 and 8

Sodium ion batteries were prepared by the same procedure as that of Examples 1 and 2 and Comparative Examples 1 and 2, except that Na metal was used for the active material layer on a counter electrode side; and polycarbonate (PC) and fluoroethylene carbonate (FEC) were mixed with each other at a ratio (PC:FEC) of 100:5 (wt %), and the mixture was further mixed with 1M NaPF$_6$ to prepare an electrolytic solution.

Examples 9 and 10, Comparative Example 9 and 10

Sodium ion batteries were prepared by the same procedure as that of Examples 1 and 2 and Comparative Examples 1 and 2, except that Na metal was used for the active material layer on a counter electrode side; and ethylene carbonate (EC) and dimethyl carbonate (DMC) were mixed with each other at a ratio (EC:DMC) of 100:5 (wt %), and the mixture was further mixed with 1M NaN(CF$_3$SO$_2$)$_2$ to prepare an electrolytic solution.

[Evaluation 2]

(Evaluation of Capacity Retention of Sodium Ion Battery)

The sodium ion batteries were driven under the following conditions.

Charging: CC 3.6 V 1 C (220 mAh/g=1 C)
Discharging: CC 0.6 V 1 C (220 mAh/g=1 C)
Temperature: 25° C.

As shown in Table 2, the following results were obtained. In Examples 5 and 6, the capacity retention was improved as compared to Comparative Examples 5 and 6. In Examples 7 to 10 in which the material of the electrolytic solution was changed, the capacity retention was improved as compared to Comparative Examples 7 to 10. In addition, in Comparative Examples 5 to 10, the color of the separator after battery decomposition was changed; whereas, in Examples 5 to 10, the color of the separator after battery decomposition was not changed. As a result, in Comparative Examples 5 to 10, the active material was eluted to the electrolytic solution; whereas, in Examples 5 to 10, the active material was not eluted to the electrolytic solution. The capacity retention values shown in Table 2 are the value obtained after 100 cycles.

| | Active Material Layer | | | Capacity | Change of Color of Separator |
|---|---|---|---|---|---|
| | Working Electrode Side | Counter Electrode Side | Electrolytic Solution | Retention (%) | after Battery Decomposition |
| Example 5 | (COONa)$_3$-TOT | Na Metal | EC + DEC, 1M NaPF$_6$ | 93 | Not Changed |
| Example 6 | (COOLi)$_3$-TOT | | | 88 | |
| Comparative Example 5 | Br$_3$-TOT | | | 63 | Changed |
| Comparative Example 6 | Cl$_3$-TOT | | | 55 | |
| Example 7 | (COONa)$_3$-TOT | | PC + FEC, 1M NaPF$_6$ | 88 | Not Changed |
| Example 8 | (COOLi)$_3$-TOT | | | 84 | |
| Comparative Example 7 | Br$_3$-TOT | | | 64 | Changed |
| Comparative Example 8 | Cl$_3$-TOT | | | 57 | |
| Example 9 | (COONa)$_3$-TOT | | EC + DMC, 1M NaN(CF$_3$SO$_2$)$_2$ | 86 | Not Changed |
| Example 10 | (COOLi)$_3$-TOT | | | 82 | |
| Comparative Example 9 | Br$_3$-TOT | | | 63 | Changed |
| Comparative Example 10 | Cl$_3$-TOT | | | 57 | |

What is claimed is:
1. An active material used for a sodium ion battery or a lithium ion battery, the active material comprising:

(COONa)$_3$-trioxotriangulene represented by the following Formula (1) or (COOLi)$_3$— trioxotriangulene represented by the following Formula (2), wherein

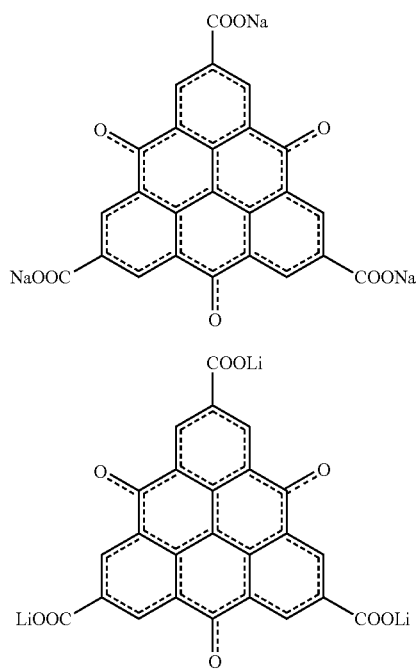

in Formulae (1) and (2), a double line including a solid line and a broken line represents a single bond or a double bond.

2. A sodium ion battery comprising:
a positive electrode active material layer containing a positive electrode active material;
a negative electrode active material layer containing a negative electrode active material; and
an electrolyte layer formed between the positive electrode active material layer and the negative electrode active material layer,
wherein the positive electrode active material or the negative electrode active material is the active material according to claim 1.

3. A lithium ion battery comprising:
a positive electrode active material layer containing a positive electrode active material;
a negative electrode active material layer containing a negative electrode active material; and
an electrolyte layer formed between the positive electrode active material layer and the negative electrode active material layer,
wherein the positive electrode active material or the negative electrode active material is the active material according to claim 1.

* * * * *

UNITED STATES PATENT AND TRADEMARK OFFICE
CERTIFICATE OF CORRECTION

PATENT NO. : 9,725,396 B2  
APPLICATION NO. : 14/730650  
DATED : August 8, 2017  
INVENTOR(S) : Yasushi Morita and Shinji Nakanishi Page 1 of 1

It is certified that error appears in the above-identified patent and that said Letters Patent is hereby corrected as shown below:

In the Specification

In Column 1, Line 48, delete "Bra-trioxotriangulene" and insert -- $Br_3$-trioxotriangulene --, therefor.

In Column 14, Line 60, delete "Bra-TOT" and insert -- $Br_3$-TOT --, therefor.

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*